United States Patent [19]
Leschinsky

[11] Patent Number: 5,413,549
[45] Date of Patent: May 9, 1995

[54] DEVICES AND METHODS FOR EFFICIENT INTRA-AORTIC BALLOON PUMPING

[75] Inventor: Boris Leschinsky, Waldwick, N.J.

[73] Assignee: Datascope Investment Corp., Montvale, N.J.

[21] Appl. No.: 132,965

[22] Filed: Oct. 7, 1993

[51] Int. Cl.⁶ .......................................... A61N 1/362
[52] U.S. Cl. ..................................................... 600/18
[58] Field of Search ................................... 600/16–18; 623/3; 604/96–99

[56] References Cited

U.S. PATENT DOCUMENTS

5,158,529  10/1992  Kanai .................................... 600/18
5,300,017   4/1994  Isoyama et al. ...................... 600/18

Primary Examiner—Lee S. Cohen
Assistant Examiner—John P. Lacyk
Attorney, Agent, or Firm—Fitzpatrick, Cella, Harper & Scinto

[57] ABSTRACT

Devices and methods are provided which involve an improved intra-aortic balloon structure. A safety balloon or safety membrane is mounted within an extension catheter. Helium contained in the safety balloon or membrane can be driven into and out of an intra-aortic balloon by forcing driving fluid into and out of the extension catheter, thereby compressing and decompressing the safety balloon or membrane. A variety of structures are suggested for insuring that the balloon or membrane does not inadvertently block the helium or drive fluid as it moves.

16 Claims, 5 Drawing Sheets

DEVICES AND METHODS FOR EFFICIENT INTRA-AORTIC BALLOON PUMPING

BACKGROUND OF THE INVENTION

1. Field of the Invention

This invention relates generally to cardiopulmonary support equipment, and more particularly, to intra-aortic balloon pumping devices in which a working fluid is used to selectively inflate and deflate the intra-aortic balloon.

2. Description of the Related Art

Intra-aortic balloon catheters are used to reduce the burden on a still-beating human heart, or to force blood to flow to arteries, for example, the coronary arteries, which are not receiving an adequate blood supply.

Intra-aortic balloon catheters typically consist of an intra-aortic balloon ("IAB"), an extension catheter, and a connecting catheter which joins the balloon and the extension catheter. The extension catheter, connecting catheter, and balloon are in fluid communication so that forcing gas through the connecting catheter causes the IAB to inflate and removing gas through connecting catheter causes the IAB to deflate.

IAB catheters can be positioned in a patient's body using minimally-invasive catheterization procedures, rather than surgery. Typically, the furled intra-aortic balloon is inserted through a puncture wound in the groin into the patient's femoral artery, and is advanced until it is disposed within the patient's descending aorta. Now, the heart can be assisted by inflating and deflating the IAB in counterpulsation to the beating heart.

In designing IAB's, a consideration is the benefits of minimizing the size of the catheters (both extension and connecting) which are used to inflate and deflate the intra-aortic balloon. Since the connecting catheter passes through the patient's arterial system, it is important that there be as much clearance as possible around that catheter for healthy blood flow. If too large a catheter is used, this may interfere with proper blood circulation past the catheter. If, however, a narrow catheter is used, it becomes more difficult to shuttle gas through the catheter to inflate and deflate the balloon. The gas most commonly used in IAB systems is helium because of its low molecular weight and consequent low flow resistance.

To minimize the amount of helium which could enter the patient's body in the event of a leak and to guard against overinflating the balloon, it is known to contain the helium in a closed, fixed-volume system consisting of the intra-aortic balloon, the extension catheter, the connecting catheter joining the balloon and extension catheter and a reservoir. The extension catheter is attached at its proximal end to a fixed-volume structure divided into two chambers, a reservoir chamber and a pumping chamber, by a medial inner membrane. A volume of helium is contained in the reservoir chamber which is isolated from the pumping chamber. Thus, the helium is contained within the reservoir/extension catheter/connecting catheter/balloon system. Inflation and deflation is accomplished by shuttling the helium between the intra-aortic balloon on one end and the reservoir chamber on the other. Alarm and monitoring systems can be provided to detect any breaks, kinks or other obstructions in the helium flow bath, and these systems can operated by detecting the pressure of the helium.

The pumping chamber of the fixed-volume structure is connected to a system for controllably pressurizing and depressurizing that chamber. By filling the pumping chamber of the fixed volume structure with air, or any other fluid, the pressure in that chamber increases, causing the medial inner membrane to reduce the volume of the reservoir chamber. This compresses the helium in the closed system, and causes the helium to flow through the extension catheter, through the connecting catheter and into the intra-aortic balloon. To deflate the intra-aortic balloon, the pumping chamber of the fixed volume structure is depressurized, and the gas flow reverses.

Two different fixed volume structures are known for use in an IAB catheter system. In the first, the fixed volume structure is cylindrical in shape, and consists of a rigid, fluid-impervious outer shell (the "safety chamber") which serves as the pumping chamber, and an enclosed, cylindrical collapsible balloon (the "safety chamber balloon") which acts as the reservoir chamber. The safety chamber balloon is attached in fluid-tight fashion to the lumen of the extension catheter. To drive the IAB catheter, pressurized fluid (typically, a gas) can be shuttled into and out of the safety chamber. When inflating the IAB, fluid flows into the safety chamber, and as pressure increases in the safety chamber, the enclosed safety chamber balloon collapses, forcing helium toward the IAB balloon.

To deflate the IAB, fluid is evacuated from the safety chamber. This causes the pressure in the shell to drop, and so helium flows out of the IAB balloon and into the connecting catheter as the safety chamber balloon inflates.

The other type of fixed volume structure is known as a safety disk. As with the safety chamber, a flexible membrane is used, but in the case of a safety disk, the membrane takes the form of a medial membrane which divides the rigid outer shell into separate reservoir and pumping chambers. The reservoir chamber of the safety disk communicates with the extension catheter, and is part of the system which contains the helium, while the pumping chamber is connected to a pressuring and depressurizing device. The medial membrane isolates the two chambers from one another so that when the pumping chamber is pressurized, helium gas flows into the intra-aortic balloon, and vice versa.

The present invention improves over both the safety chamber and safety disk devices in that it reduces the amount of working fluid (gas) which is contained in the closed system. It also reduces the volume of compressed gas which is needed to inflate and deflate the IAB.

Other benefits obtained by using the present invention are reductions in the size of the vacuum and pressure tanks required, faster inflation and deflation, reduced noise and a reduction in the size of the drive system. In addition, it is possible to monitor visually operation of the device.

Still other benefits which can be obtained by using the present invention relate to an increase in sensitivity of the alarm and monitoring functions of the IAB drive system (again, it is known in the art to monitor the pressure in the helium-filled system to detect breaks or kinks in the helium-filled IAB/connecting catheter system). Since elimination of the safety disk/chamber reduces the volume of the sealed helium, this means that variations in gas pressure which would signify breaks or blockages in the helium path would not be as attenuated as in the larger-volume system (less helium is present, so there is less gas to attenuate (dampen) a pressure change). Accordingly, the present invention can facilitate monitoring of the IAB gas pressure.

Another benefit of the present invention is also due to the reduction in the volume of helium gas which is needed. It is estimated that the present invention uses about half the volume of helium as do known devices (i.e., 40 cc compared with 80 cc). Therefore, any changes in balloon volume due to external pressure changes (i.e., the patient is turned, patient blood pressure changes, or atmospheric pressure varies) will be proportionate to the balloon volume. For example, if the patient's blood pressure drops and a conventional 80 cc IAB system sees IAB expansion of 1 cc, the reduced volume of the present system, 40 cc, will only expand by about $\frac{1}{2}$ cc. Thus, in the instant invention, any such incidental changes in IAB volume will have much less of an effect on the volume of blood pumped by the IAB.

All of the foregoing benefits can be obtained by utilizing the devices and methods described below.

SUMMARY OF THE INVENTION

The present invention involves a reduced volume intra-aortic balloon catheter (or catheter assembly) having an intra-aortic balloon defining a balloon chamber, a connecting catheter having a connecting catheter lumen, this connecting catheter lumen being in fluid communication with the balloon chamber, and an extension catheter having an extension catheter lumen and an extension catheter lumen inner wall, the extension catheter lumen having proximal and distal ends. A safety balloon is positioned in the extension catheter lumen, this safety balloon defining a safety balloon chamber and having working fluid therein, the safety balloon chamber communicating with the connecting catheter lumen. When drive fluid is introduced between the extension catheter lumen inner wall and the safety balloon, the safety balloon collapses, urging working fluid into the connecting catheter and from that connecting catheter into the intra-aortic balloon, inflating the intra-aortic balloon (the safety balloon can either fully or partially occupy the extension catheter lumen).

In another embodiment of this reduced volume intra-aortic balloon catheter (or catheter assembly), the safety balloon is replaced by a flexible safety membrane disposed in the extension catheter lumen and sealingly attached to the extension catheter lumen inner wall. The flexible safety membrane thereby divides the extension catheter lumen into first and second regions, the first region being in fluid communication with the fluid pressure source and the second region having a working fluid therein and being in fluid communication with the connecting catheter lumen. When a drive fluid is introduced from the fluid pressure source into the first region, the safety membrane moves, causing the second region to decrease in volume, thereby causing working fluid in the second region to enter the connecting catheter lumen. Structures can be provided which insure that fluids can flow freely into and out of the two regions.

Another embodiment of this invention relates to a method for selectively driving an IAB catheter, involving the steps of providing an intra-aortic balloon defining a balloon chamber, a connecting catheter having a connecting catheter lumen, that connecting catheter lumen being in fluid communication with the balloon chamber, and an extension catheter having an extension catheter lumen and an extension catheter lumen inner wall, this extension catheter having proximal and distal ends. The proximal end of the extension catheter is attached to pressurizing/depressurizing means and the distal end of the extension catheter is attached to the connecting catheter, while a flexible safety membrane is disposed in the extension catheter lumen. The flexible membrane thereby divides the extension catheter lumen into first and second regions. The second region has a working fluid therein and is in fluid communication with the connecting catheter lumen through the distal end while the first region is in fluid communication with the pressurizing/depressurizing means. By selectively introducing drive fluid into the first region, thereby causing the first region to increase in volume, and in turn causing that safety membrane to move, the second region decreases in volume, so that the working fluid in the second region enters the connecting catheter lumen. Selectively evacuating drive fluid from the first region causes the first region to decrease in volume, and the second region to increase in volume, and the working fluid to move from the connecting catheter lumen into the second region.

DESCRIPTION OF THE PREFERRED EMBODIMENTS

The present invention is intended to improve the performance of intra-aortic balloon catheters. Briefly, one utilizing the present invention can obtain these benefits because of the manner in which this invention drives the intra-aortic balloon (IAB) used to assist a weakened heart. One benefit of this invention is that the intra-aortic balloon can be inflated and deflated more easily, and more rapidly, than in conventional devices.

An IAB catheter enables a medical practitioner to alternately inflate and deflate an intra-aortic balloon disposed within a patient's aorta, in counterpulsation to the beating heart. Such inflation and deflation of the IAB will reduce the load on the beating heart, because the inflation of the balloon and then deflation immediately prior to systole reduces the back pressure against which the heart must pump blood during systole.

The IAB is controllably inflated and deflated by filling and then removing a gas from it. Currently, the gas of choice is helium.

Figure 1:
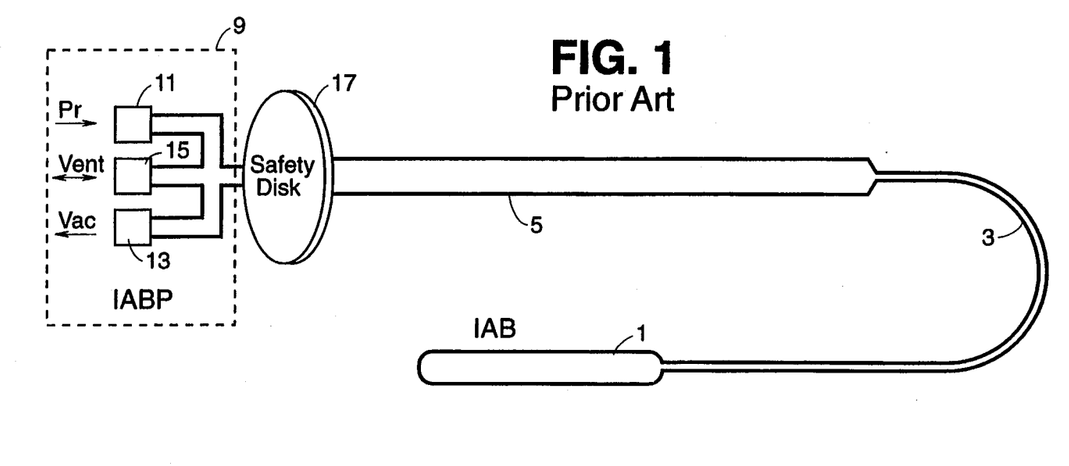
FIG. 1 is a plan side view of a conventional intra-aortic balloon catheter assembly with a safety disk.
Figure 2:
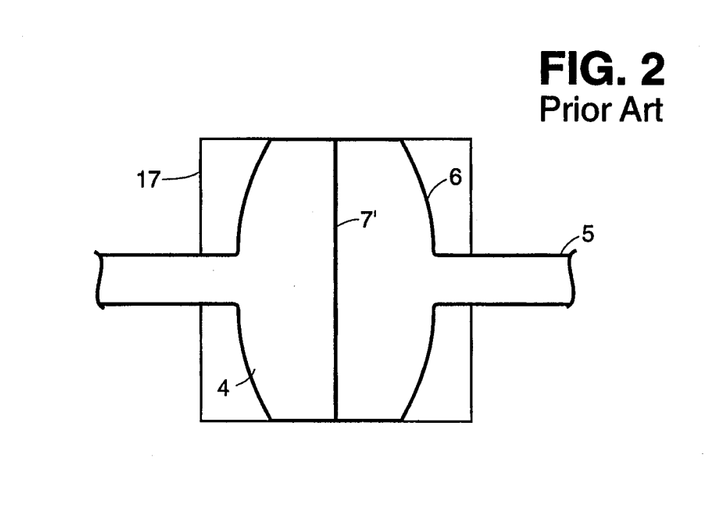
FIG. 2 is a side cross-sectional view of a safety disk structure.

A conventional IAB catheter, along with a driving device, is shown in FIGS. 1 and 2. Gas drive system 9 serves to alternately inflate and deflate the intra-aortic balloon 1. The gas drive system 9 communicates with the IAB 1 via a safety disk 17, which in turn communicates with an extension catheter 5. Extension catheter 5 communicates with the IAB 1 via a connecting catheter 3.

When implanted in a patient, the connecting catheter 3 runs into the patient's body, the distal end of the connecting catheter communicates with the intra-aortic balloon 1, which is positioned in the patient's body in the aorta.

The drive system 9 contains a pressurized gas source 11, a vacuum source 13, and a vent 15. A control mechanism (not shown) selectively connects each of these sources to the safety disk 17.

As previously explained, safety disk 17 contains a deformable medial membrane 7' which isolates the helium in the extension catheter/connecting catheter/intra-aortic balloon system from the drive system 9. Thus, when the pressurized gas source 11 drives gas into the safety disk, the drive gas enters the pumping chamber 4 on one side of the safety disk, deforming the membrane 7' so as to reduce the volume of the reservoir chamber 6 on the other side of that membrane. This reduction in volume drives helium gas from the safety disk through the extension and connecting catheters toward the intra-aortic balloon.

Conversely, when the vacuum source 13 is joined to the safety disk 17, the membrane is drawn in the other direction, reducing the volume of the pumping chamber on the drive (proximal) side of membrane 7. Since the volume of reservoir chamber 6 on the other (distal) side of the membrane is correspondingly increased, helium now flows out of the IAB and into the safety disk.

The present invention improves on known intra-aortic balloon technology by providing a structure which reduces both the volume of working gas sealed in the IAB catheter and the volume of driving gas needed to inflate and deflate the balloon.

Although henceforth the gas sealed in the IAB device will be identified as helium, and the driving gas as air, other fluids could also be used.

In order to keep separate the air used to drive the IAB catheter from the helium contained in the closed system, the present invention provides the extension catheter with an internal isolating membrane. This isolating membrane serves to keep the working gas, generally helium, which serves to inflate and deflate the IAB, separate from the drive gas, generally air, provided by the drive system.

As explained in greater detail below, by filling the appropriate portion of the extension catheter with air, the helium isolated on the other side of the membrane can be forced from the extension catheter through the connecting catheter, and into the IAB. If the dimensions of the various IAB catheter components are chosen correctly, very littler, or even no helium will remain in the extension catheter when the IAB is fully distended Thus there is minimal "dead space", unlike known devices, where the extension catheter remains filled with helium at all times, even after the IAB is inflated.

It will be appreciated that in this invention, one of the functions performed by the extension catheter and membrane is to isolate the helium used to inflate and deflate the IAB from the pressurized/depressurized air supply.

The membrane in this invention is incorporated as part of the extension catheter structure. The membrane and extension catheter structures are also constructed in a manner which improves the performance of this invention, and which is not known.

This improvement is possible because the extension catheter, which was previously "dead space" only serving the purpose of joining the gas supply lines to the connecting catheter, now serves the dual functions previously performed by the connecting catheter and by the safety chamber/disk. For example, to drive a 40 cc intra-aortic balloon, known IAB catheter designs require approximately 100 cc of helium, whereas the present invention needs only about 53 cc of helium. Moreover, in addition to using less helium to inflate the same size balloon as the known devices, the present invention does so while only filling and evacuating from the extension catheter some 45–55 cc of compressed air. In contrast, known devices use some 65–75 cc of compressed air.

FIGS. 3–5A show a first embodiment of the present invention. In this embodiment, the cylindrical intra-aortic balloon 1 is connected in fluid-tight manner to a connecting catheter 3, and that connecting catheter is in turn joined in fluid-tight manner to the distal end of sausage-shaped balloon 7. The sausage-shaped balloon 7 is completely enclosed within the extension catheter lumen 18 of extension catheter 5, and is made of non-distensible material. The safety balloon 7 in this embodiment is the isolating membrane which separates the drive gas, air, from the working gas, helium.

The extension catheter 5 and sausage-shaped balloon 7 can be dimensioned and disposed such that even when the balloon 7 is fully inflated, it still will not completely fill the extension catheter lumen 18. The balloon 7 can be held in the extension catheter lumen 18 in a manner such that it will not block gas flowing between the driving device 9 and the extension catheter lumen 18, or between the connecting catheter 3 and the chamber of the sausage-shaped balloon.

Again, the sausage-shaped balloon 7, connecting catheter 3, and the IAB 1 together form a sealed system which contains a fixed amount of helium, or some other suitable fluid.

The proximal end of the connecting catheter is attached to a driving device 9 having a pressurized air supply 11, a vacuum supply 13, and a vent 15. This way, the extension catheter lumen 18 can be pressurized and depressurized with air, as desired.

Figure 3:
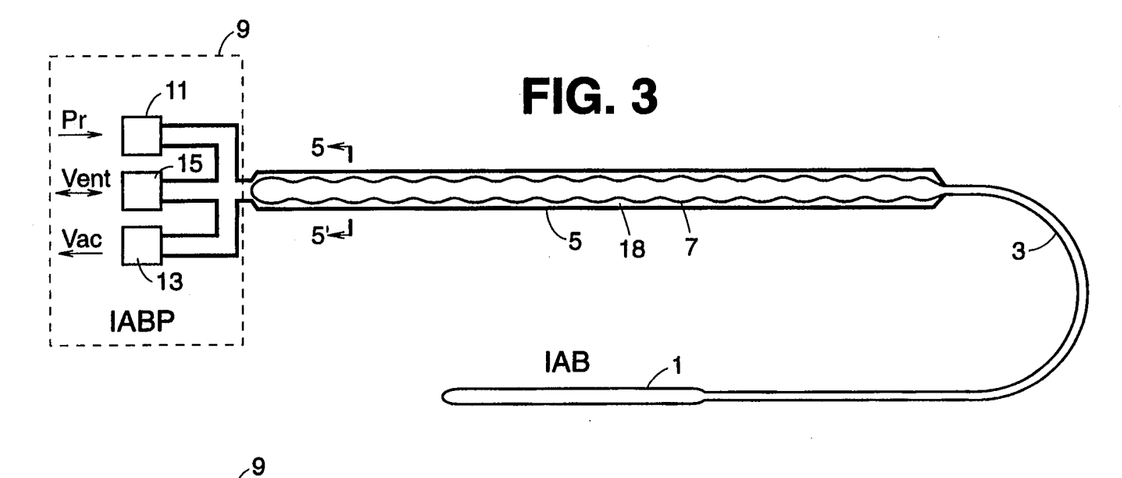
FIG. 3 is a side cross-sectional view of a first embodiment of the invention.

FIG. 3 shows this embodiment as it appears when the IAB is deflated. In this case, the vacuum supply 13 is in communication with the extension catheter lumen 18, and so at least some of the air in the extension catheter lumen surrounding the sausage-shaped balloon 7 is withdrawn. This reduces the pressure inside the extension catheter lumen, causing balloon 7 to inflate. In response to the expansion of the balloon 7, helium leaves the IAB 1, and the IAB deflates.

Figure 4:
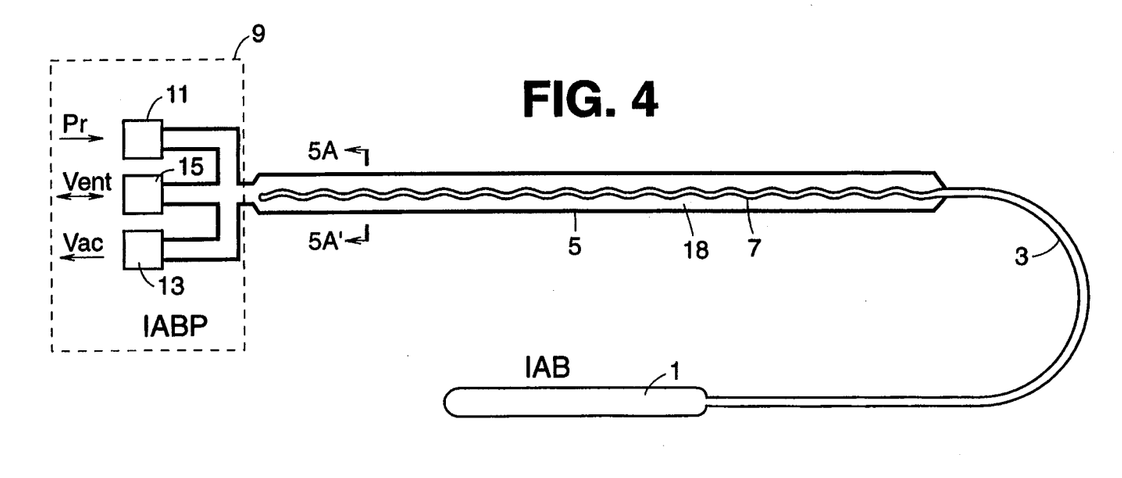
FIG. 4 is another side cross-sectional view of a first embodiment of the invention.
Figure 5:
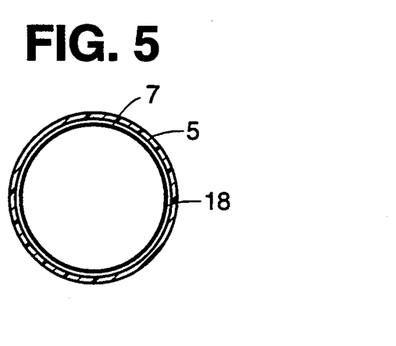
FIG. 5 is a cross-sectional view along line 5–5' of FIG. 3 when the intra-aortic balloon is deflated.
Figure 5A:
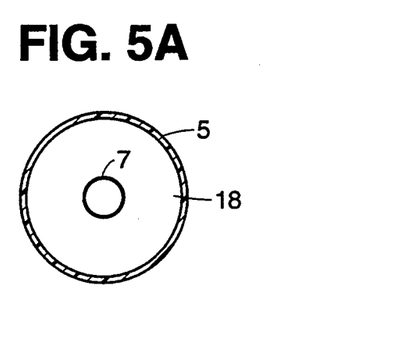
FIG. 5A is a cross-sectional view along line 5A–5A' of FIG. 4 when the intra-aortic balloon is inflated.

FIG. 4 shows this embodiment as it appears when the IAB is inflated. Now, the pressurized air supply 11 is in communication with the extension catheter lumen, and the extension catheter lumen 18 is pressurized. This causes the sausage-shaped balloon 7 to deflate, and as the balloon 7 collapses, the helium contained therein flows into connecting catheter 3, inflating IAB 1.

It is preferable to constrain the sausage-shaped balloon 7 in the extension catheter lumen 18 in a manner such that the balloon will not block air flow into or out of the extension catheter lumen, and also such that helium will be able to flow into and out of the balloon 7 without obstruction.

Several particularly preferred embodiments of this invention will now be described. These embodiments are all constructed in a manner which will prevent interference with the flow of either the helium or the air.

Figure 6:
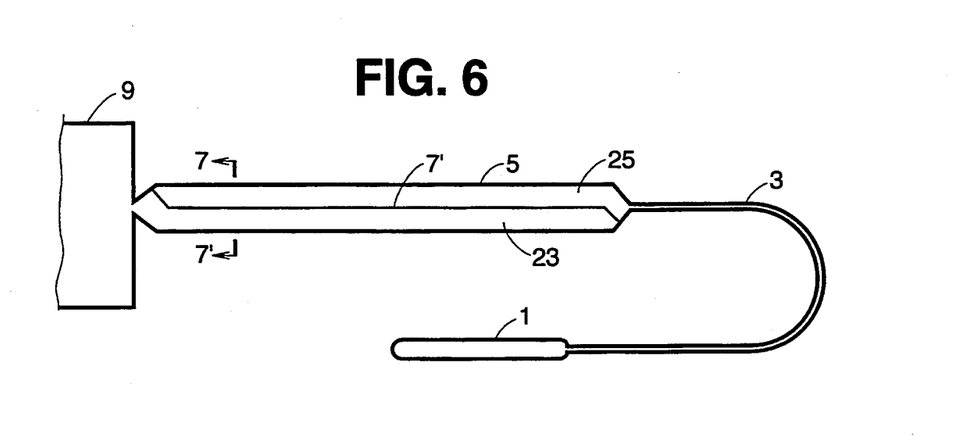
FIG. 6 is a top cross-sectional view of a second embodiment of the invention.
Figure 7:
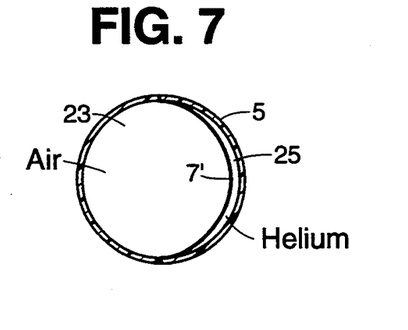
FIG. 7 is a cross-sectional view along line 7–7' of FIG. 6 when the intra-aortic balloon is inflated with gas.
Figure 7A:
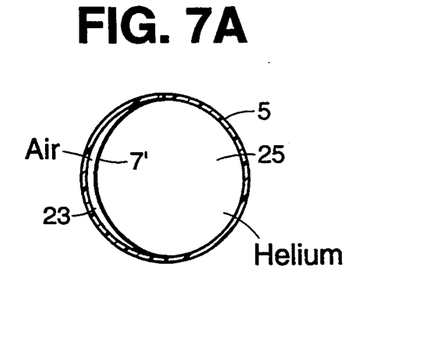
FIG. 7A is a cross-sectional view along line 7–7' of FIG. 6 when the intra-aortic balloon is deflated.

For example, FIGS. 6–7A depict an IAB device in which a membrane 7' is held within the extension catheter 5. This membrane 7' is a rectangular sheet joined in fluid-impervious fashion along its entire top and bottom lengths to the inner wall of extension catheter 5. Likewise, the proximal and distal ends of the membrane 7' are attached to the proximal and distal ends of the extension catheter. As shown in FIG. 6, the membrane 7' thereby serves to divide the extension catheter lumen 18 into two separate chambers. One chamber 23 communicates only with the driving device, while the other chamber 25 only communicates with the connecting catheter. The membrane 7' separates chambers 23 and 25 so that gas flowing into one chamber does not mix with gas flowing into the other chamber.

Preferably, membrane 7' is dimensioned so that regardless of its position, some space always remains between the membrane and the nearest part of the inside wall of the extension catheter. This remaining space insures that the membrane will not interfere with gas flow through either chamber 23 or 25.

When pressurized air flows into chamber 23, the volume of chamber 23 increases, and the membrane 7' moves toward the other chamber 25. As chamber 25 shrinks, helium contained therein flows toward and causes inflation of the IAB 1. Alternatively, when air is evacuated from chamber 23, chamber 23 now shrinks, and the membrane 7' shifts accordingly. Since chamber 25 now increases in volume, helium flows from connecting catheter 3 into chamber 27 and[from the IAB 1 into the connecting catheters, thereby causing the IAB to deflate.

Figure 8:
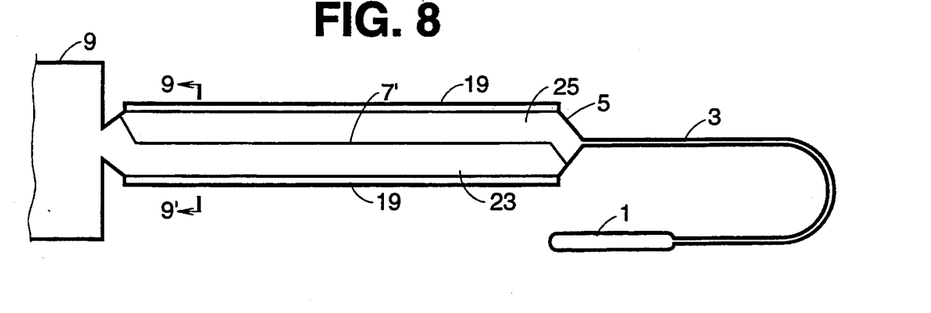
FIG. 8 is a top cross-sectional view of a third embodiment of the invention.
Figure 9:
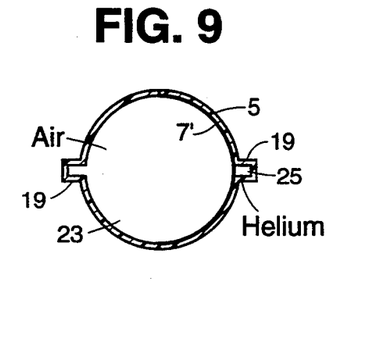
FIG. 9 is a cross-sectional view along line 9–9' of FIG. 8 when the intra-aortic balloon is inflated with gas.
Figure 9A:
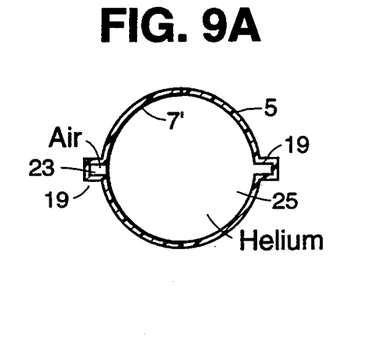
FIG. 9A is a cross-sectional view along line 9–9' of FIG. 8 when the intra-aortic balloon is deflated.

Another embodiment of the present invention is depicted in FIGS. 8–9A. This embodiment resembles the previously-discussed embodiment in that membrane 7' is disposed in the center of the extension catheter 5, and is attached along its top and bottom lengths to the inner wall of the extension catheter. However, membrane 7' is now dimensioned such that when either chamber 23 or 25 is full of gas, the membrane 7' will completely contact the inner wall of the extension catheter 5.

Gas flow through the chambers 23 and 25 is assured even when the membrane 7' contacts the entire inner surface of the extension catheter 5 because the extension catheter 5 is provided with side channels 19 in the catheter wall. Each chamber 23 and 25 has one channel associated therewith (more than one channel, and other channel shapes and patterns might also be used). Each of these channels 19 serves as a passageway through which gas can pass even after the membrane 7' is in full-contact with the inner wall of the extension catheter. Channels 19 prevent trapping gas between the membrane and the inner wall of the extension catheter.

Figure 10:
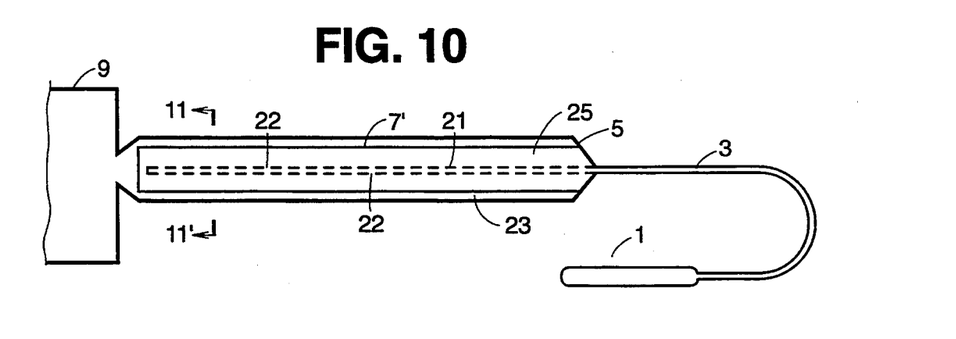
FIG. 10 is a top cross sectional view of a fourth embodiment of the invention.
Figure 11:
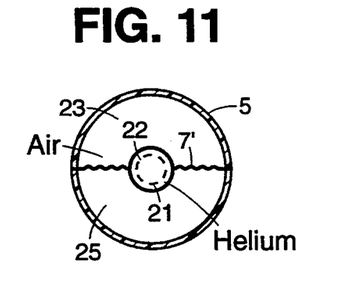
FIG. 11 is a cross-sectional view along line 11–11' of FIG. 10 when the intra-aortic balloon is inflated with gas.
Figure 11A:
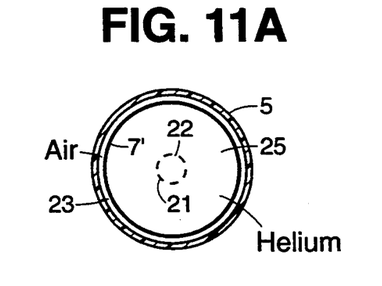
FIG. 11A is a cross-sectional view along line 11–11' of FIG. 10 when the intra-aortic balloon is deflated.

Still another embodiment of this invention is illustrated in FIGS. 10–11A. Here, a non-collapsible inner tube 21 is provided within extension catheter 5. Table 21 and catheter 5 are preferably, but not necessarily, co-axial. Inner tube 21 has a number of perforations 22 in its sides, or is otherwise made fluid-permeable. The distal end (toward the right in FIG. 10) of inner tube 21 is in fluid communication with the proximal end of the connecting catheter 3.

Membrane 7' is disposed within extension catheter 5, and completely surrounds inner tube 21. The distal end of the membrane is attached in fluid-impervious fashion to the distal end of the interior of the extension catheter 5.

Alternatively, membrane 7' could be joined to the inner tube 21, provided that joint is fluid-impervious and the fluid-pervious portion of the inner tube is fully-enclosed by the membrane.

The proximal end of the membrane 7' is shown as being unattached, but alternatively could be attached to the extension catheter or inner tube, provided that such attachment does not interfere with the air or helium flow.

In this embodiment of the invention, pressurized air from gas source 11 flows into the extension catheter 5, causing the membrane 7' to collapse, as seen in FIG. 11. As the membrane 7' collapses, the helium contained therein is forced into the inner tube 21 through the openings 22, and thence toward the intra-aortic balloon 1.

Should the membrane 7' collapse such that a distal portion of the membrane completely surrounds the inner tube 21 before a proximal portion collapses completely, gas located behind that collapsed region can still enter into the inner tube because the openings 22 are disposed along the length of the inner tube. The membrane continues collapsing until it completely contacts the inner tube 21, as shown in FIG. 11.

To deflate the IAB, the extension catheter is connected to the vacuum supply 13 and is thereby evacuated, causing the membrane 7' to swell. Accordingly, helium flows from the connecting catheter 3 and IAB 1 along the inner tube 21, out of the openings 22, and into the membrane, thereby deflating the IAB.

Figure 12:
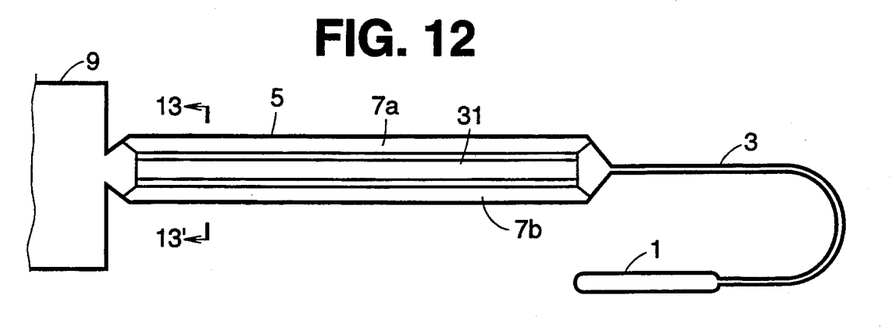
FIG. 12 is a top cross-sectional view of a fifth embodiment of the invention.
Figure 13:
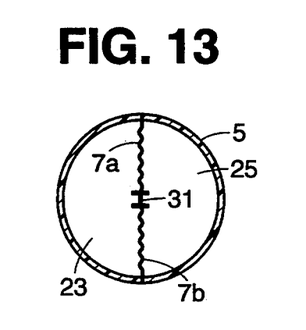
FIG. 13 is a cross-sectional view along line 13–13' of FIG. 12 when the intra-aortic balloon is partially inflated with gas.

Still another embodiment of this invention provides a structure on the movable membrane 7' for preventing obstruction of the gas flow paths by that membrane. As shown in FIGS. 12–13B, an I shaped member 31 is affixed between upper and lower membranes 7a, 7b, and those membranes are attached thereto in fluid-impervious fashion. As in the previous embodiments, membranes 7a and 7b are attached along their respective upper and lower margins to the inner wall of extension catheter 5. Again, the proximal and distal ends of each of the membranes 7a, 7b are attached in fluid-impermeable fashion to the proximal and distal ends of the extension catheter. Regardless of how the membrane 7' is disposed, there is on one side of the membrane 7' an unobstructed air path from the pressurized air supply 11 to the distal end of the extension catheter, and on the other side, an unobstructed helium path from the proximal end of the extension catheter to the connecting catheter 3. Since all of the joints in this structure are fluid-impervious, the gas on one side of the membrane 7' is isolated from that on the other.

I shaped member 31 runs for all or almost all of the length of the extension catheter 5, and serves to maintain a gas flow path regardless of the membranes position. To inflate the IAB 1, pressurized air flows into chamber 23, and as the volume of chamber 23 increases, membranes 7a, 7b and the I shaped member 31 attached thereto are urged to the right, decreasing the volume of chamber 25. As chamber 25 shrinks, helium flows therefrom into the connecting catheter 3 and into the IAB 1. Eventually, the membranes 7a, 7b will contact the inner side of the extension catheter 5; nevertheless, the helium flow path from chamber 25 will be preserved because the right portion of the I shaped member prevents the membrane 7' from obstructing the helium path.

Figure 13A:
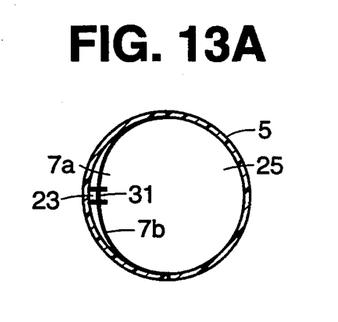
FIG. 13A is a cross-sectional view along line 13–13' of FIG. 12 when the intra-aortic balloon is inflated with gas.
Figure 13B:
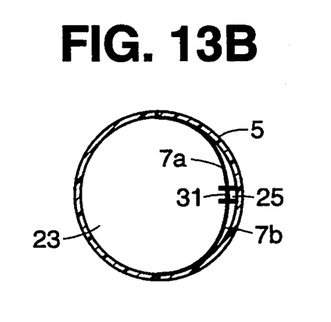
FIG. 13B is a cross-sectional view along line 13–13' of FIG. 12 when the intra-aortic balloon is deflated.

As shown in FIG. 13A, when the extension catheter is connected to the vacuum supply to deflate the IAB 1, the left side of the I shaped member prevents the membranes 7a, 7b from obstructing the air path.

It will be appreciated that the above-described embodiments of this invention can be modified so that the functions served by the two chambers are reversed. For example, with regard to the embodiment depicted in FIGS. 3–5A, the sausage-shaped balloon 7 could be connected to the driving device 9, and the space inside the extension catheter lumen 18 surrounding that balloon 7 could be filled with helium and communicate with the connecting catheter 3. By filling and emptying the balloon 7 with air, helium would be driven into and out of the connecting catheter 3, inflating and deflating IAB 1. Similarly, in the embodiment shown in FIGS. 10–11A, the driving device 9 could be attached to balloon 7, allowing chamber 25 to be filled and emptied of air. Likewise, chamber 23 surrounding balloon 7 would be filled with helium and would be in communication with connecting catheter 3, so that as air inflated and deflated balloon 7, helium would be shuttled through connecting catheter 3, inflating and deflating IAB 1.

It will also be appreciated that the terms gas and fluid have been used in interchangeable fashion, and that the present invention covers devices in which each of the drive and working fluids are gaseous or liquid.

A wide variety of materials and construction techniques can be used to assemble the aforementioned embodiments of the claimed invention. For example, the sausage-shaped balloon 7 and membranes 7', 7a and 7b can be formed of polyurethane, while the connecting catheter 3 can be made from polyethylene. The extension catheter can be constructed from PVC (polyvinyl chloride), and the IAB from polyurethane. Joints can be made using techniques such as welding or gluing. Of course any other suitable materials could be used.

The present invention improves IAB catheter performance, since it is no longer necessary to provide a helium-containing fixed-volume chamber outside of the extension catheter. By providing a balloon or membrane for isolating and containing the helium inside the extension catheter, the amount of helium needed is reduced. Accordingly, an intra-aortic balloon can be driven using only about 70% one the compressed gas required by other devices. The power required to operate this device is estimated to be only about 70% of that used in prior art devices, and so the power supply needed to drive the device can be made smaller. Moreover, the volume of the drive source pressure and vacuum tanks need only be about 70% of conventional tanks. In particular, the helium tank could be made only about half the size of a conventional tank. Balloon inflation and deflation is more rapid, since it is no longer necessary to pressurize a dead space, namely, the safety disk or the safety chamber balloon.

By eliminating the safety chamber/disk, the size of the IAB driver console can also be reduced. Lastly, since less air and helium are shuttled back and forth, the device may operate more quietly.

It will be appreciated that the present invention is not intended to be limited to the drawings and embodiments discussed above. Numerous departures in construction, materials and operation can be made therefrom while still remaining within the scope of the claimed invention.

What we claim is:

1. A reduced volume intra-aortic balloon catheter assembly, comprising:
   an intra-aortic balloon defining a balloon chamber:
   a connecting catheter having a connecting catheter lumen, said connecting catheter lumen being in fluid communication with said balloon chamber;
   an extension catheter having an extension catheter lumen and an extension catheter lumen inner wall, said extension catheter lumen having a proximal end and a distal end, said proximal end being designed for connection to a fluid pressurizing/depressurizing means, said distal end being in fluid communication with said connecting catheter lumen; and
   a safety balloon disposed in said extension catheter lumen, said safety balloon defining a safety balloon chamber and having a working fluid therein, said safety balloon chamber communicating with said connecting catheter lumen,
   wherein when a drive fluid is introduced between said extension catheter lumen inner wall and said safety balloon, said safety balloon collapses, urging said working fluid contained in said safety balloon chamber into said connecting catheter lumen and from said connecting catheter lumen into said intra-aortic balloon chamber, inflating said intra-aortic balloon.

2. A reduced volume intra-aortic balloon catheter assembly according to claim 1, further comprising:
   an inner tube having an inner tube lumen and at least one opening in a side of said inner tube, said inner tube being at least partially enclosed within said safety balloon, a distal end of said inner tube lumen being in fluid communication with a proximal end of said connecting catheter lumen,
   wherein when said working fluid is evacuated from said safety balloon chamber, said safety balloon collapses at least partially around said inner tube.

3. A reduced volume intra-aortic balloon catheter assembly for use with a fluid pressure source, comprising:
   an intra-aortic balloon defining a balloon chamber:

a connecting catheter having a connecting catheter lumen, said connecting catheter lumen being in fluid communication with said balloon chamber;

an extension catheter having an extension catheter lumen and an extension catheter lumen inner wall, said extension catheter lumen having a proximal end and a distal end, said proximal end connected to said fluid pressure source and said distal end connected to said connecting catheter lumen; and a flexible safety membrane disposed in said extension catheter lumen and sealingly attached to said extension catheter lumen inner wall, said flexible safety membrane thereby dividing said extension catheter lumen into a first region and a second region, said first region being in fluid communication with said fluid pressure source and said second region having a working fluid therein and being in fluid communication with said connecting catheter lumen, wherein when a drive fluid is introduced from said fluid pressure source into said first region, said safety membrane moves, causing said second region to decrease in volume, thereby causing said working fluid in said second region to enter said connecting catheter lumen.

4. A reduced volume intra-aortic balloon catheter assembly according to claim 3, further comprising:

fluid-path maintaining means for maintaining a first fluid path in said first region and a second fluid path in said second region, regardless of how said safety membrane is positioned.

5. A reduced volume intra-aortic balloon catheter assembly according to claim 4, wherein said fluid-path maintaining means is provided by selecting said safety membrane to be of a size such that when said first region is filled with said drive fluid said second region still has a volume of working fluid therein, and when said second region is filled with said working fluid said first region still has a volume of said drive fluid therein.

6. A reduced volume intra-aortic balloon catheter assembly according to claim 4, wherein said extension catheter lumen inner wall has at least one of a first channel formed therein and communicating with said first region, and at least one of a second channel formed therein and communicating with said second region, and said fluid-path maintaining means comprises said first and said second channels.

7. A reduced volume intra-aortic balloon catheter assembly according to claim 4, wherein said fluid-path maintaining means comprises:

an "I" shaped member, said safety membrane being attached to said "I" shaped member in such a fashion that fluid flow is maintained through at least one half of said "I" shaped member regardless of the position of said safety membrane.

8. A reduced volume catheter for joining an intra-aortic balloon to a drive fluid pressurizing/depressurizing means, comprising:

a connecting catheter having a connecting catheter lumen;

an extension catheter having a proximal end and a distal end, an extension catheter lumen and an extension catheter lumen inner wall, said extension catheter lumen being in fluid communication with said pressurizing/depressurizing means and said distal end of said extension catheter being attached to said connecting catheter lumen; and a safety balloon disposed in said extension catheter lumen, said safety balloon defining a safety balloon chamber, said safety balloon chamber having a working fluid therein and being in fluid communication with said connecting catheter lumen, wherein when a drive fluid from said pressurizing/depressurizing means is introduced between said extension catheter lumen inner wall and said safety balloon, said safety balloon collapses, urging said working fluid contained within said safety balloon chamber into said connecting catheter lumen.

9. A reduced volume catheter according to claim 8, further comprising:

an inner tube having an inner tube lumen and at least one opening in a side of said inner tube, said inner tube being at least partially enclosed within said safety balloon, a distal end of said inner tube lumen being in fluid communication with a proximal end of said connecting catheter lumen, wherein when said working fluid is evacuated from said safety balloon chamber, said safety balloon collapses at least partially around said inner tube.

10. A reduced volume catheter for joining an intra-aortic balloon to a drive fluid pressuring/depressurizing means, comprising:

a connecting catheter having a connecting catheter lumen;

an extension catheter having a proximal end and a distal end, an extension catheter lumen and an extension catheter lumen inner wall, said extension catheter lumen being in fluid communication with said pressurizing/depressurizing means and said distal end being connected to said connecting catheter lumen; and a safety membrane disposed in said extension catheter lumen and sealingly attached to said extension catheter lumen inner wall, said safety membrane thereby dividing said extension catheter lumen into a first region and a second region, said second region having a working fluid therein and being in fluid communication with said connecting catheter lumen through said distal end of said extension catheter, wherein when a drive fluid from said pressurizing/depressurizing means is introduced into said first region said safety membrane moves, causing said second region to decrease in volume, and causing said working fluid in said second region to enter said connecting catheter lumen.

11. A reduced volume catheter assembly according to claim 10, further comprising:

fluid-path maintaining means for maintaining a first fluid path in said first region and a second fluid path in said second region, regardless of how said safety membrane is positioned.

12. A reduced volume catheter according to claim 11, wherein said fluid-path maintaining means is provided by selecting said safety membrane to be of a size such that when said first region is filled with said drive fluid said second region still has a volume of working fluid therein, and when said second region is filled with said working fluid said first region still has a volume of said drive fluid therein.

13. A reduced volume catheter according to claim 11, wherein said extension catheter lumen inner wall has at least one of a first channel formed therein and communicating with said first region, and at least one of a second channel formed therein and communicating with said second region, and said fluid-path maintaining means comprises said first and said second channels.

14. A reduced volume catheter according to claim 11, wherein said fluid-path maintaining means comprises:
an "I" shaped member, said safety membrane being attached to said "I" shaped member in such a fashion that fluid flow is maintained through at least one half of said "I" shaped member regardless of a position of said safety membrane.

15. A method for selectively driving an intra-aortic balloon catheter from a drive fluid pressurizing/depressurizing means, comprising the steps of:
providing an intra-aortic balloon defining a balloon chamber, a connecting catheter having a connecting catheter lumen, said connecting catheter lumen being in fluid communication with said balloon chamber, and an extension catheter having an extension catheter lumen and an extension catheter lumen inner wall, said extension catheter having a proximal end and a distal end, said proximal end of said extension catheter being attached to said pressurizing/depressurizing means and said distal end of said extension catheter being attached to said connecting catheter, and a flexible safety membrane disposed in said extension catheter lumen, said flexible membrane thereby dividing said extension catheter lumen into a first region and a second region, said second region having a working fluid therein and being in fluid communication with said connecting catheter lumen through said distal end and said first region being in fluid communication with said pressurizing/depressurizing means;
selectively introducing a drive fluid into said first region, causing said first region to increase in volume and causing said safety membrane to move, in turn causing said second region to decrease in volume, and causing said working fluid in said second region to enter said connecting catheter lumen, and thereby inflating said intra-aortic balloon; and
selectively evacuating said drive fluid from said first region, thereby causing said first region to decrease in volume, said second region to increase in volume, and said working fluid to move from said intra-aortic balloon through said connecting catheter lumen into said second region.

16. A method according to claim 15, further comprising the step of providing fluid path maintaining means for maintaining a first fluid path in said first region and a second fluid path in said second region, regardless of how said safety membrane is positioned.

* * * * *

UNITED STATES PATENT AND TRADEMARK OFFICE
CERTIFICATE OF CORRECTION

PATENT NO. : 5,413,549

DATED : May 9, 1995

INVENTOR : BORIS LESCHINSKY

It is certified that errors appear in the above-identified patent and that said Letters Patent is hereby corrected as shown below:

COLUMN 1

Line 23, "connecting" should read --the connecting--;

Line 66, "bath," should read --path,--; and

Line 67, "operated" should read --operate--.

COLUMN 4

Line 51, "cross sectional" should read --cross-sectional--.

COLUMN 5

Line 55, "membrane 7." should read --membrane 7'.--.

COLUMN 6

Line 13, "littler," should read --little,--;

Line 14, "distended" should read --distended.--; and

Line 15, "Thus" should read --Thus,--.

COLUMN 7

Line 60, "chamber 27" should read --chamber 25--; and "and[from" should read --and from--.

COLUMN 8

Line 18, "Table" should read --Inner tube--; and

UNITED STATES PATENT AND TRADEMARK OFFICE
CERTIFICATE OF CORRECTION

PATENT NO. : 5,413,549

DATED : May 9, 1995

INVENTOR : BORIS LESCHINSKY

It is certified that errors appear in the above-identified patent and that said Letters Patent is hereby corrected as shown below:

COLUMN 8, Cont'd.

Line 31, "joint" should read --the joint--.

COLUMN 9

Line 15, "membranes" should read --membrane's--.

COLUMN 10

Line 3, "one" should read --of--; and

Line 68, "chamber:" should read --chamber;--.

COLUMN 12

Line 47, "assembly" should be deleted.

Signed and Sealed this

Ninth Day of April, 1996

Attest:

BRUCE LEHMAN

Attesting Officer

Commissioner of Patents and Trademarks